United States Patent [19]

Breslow et al.

[11] 4,323,512

[45] Apr. 6, 1982

[54] PROCESS FOR THE PREPARATION OF STEROIDAL 17α-ARYLCARBOXYLATES

[75] Inventors: Ronald C. D. Breslow, Englewood, N.J.; Craig S. Wilcox, New York, N.Y.

[73] Assignee: Schering Corporation, Kenilworth, N.J.

[21] Appl. No.: 263,323

[22] Filed: May 13, 1981

[51] Int. Cl.³ .................................................. C07J 1/00
[52] U.S. Cl. ................................................. 260/397.47
[58] Field of Search ........................ 260/397.47, 397.45

[56] References Cited

U.S. PATENT DOCUMENTS 4,252,719 2/1981 Breslow et al. ................. 260/397.45
4,260,464 4/1981 Kerb et al. ....................... 260/397.45

Primary Examiner—Elbert L. Roberts
Attorney, Agent, or Firm—Anita W. Magatti; Mary S. King

[57] ABSTRACT

17-Arylcarboxylate esters of 9,11-unsubstituted 4-pregnene-17α,21-diol-3,20-diones are prepared by reaction of the corresponding 17α-hydroxy derivative with alkyl lithium and an anhydride or acyl halide reagent in the presence of 4-(di-lower alkyl)aminopyridine at low temperatures. A preferred mode of the process is the preparation of 16β-methyl-1,4-pregnadiene-17α,21-diol3,20-dione 17α-m-iodobenzoate 21-benzoate, a valuable intermediate in the manufacture of betamethasone.

5 Claims, No Drawings

PROCESS FOR THE PREPARATION OF STEROIDAL 17α-ARYLCARBOXYLATES

BACKGROUND OF INVENTION

1. Field of Invention

This invention relates to a novel esterification process. More specifically, this invention relates to a process for the direct esterification of a 17α-hydroxy group in a steroid bearing the dihydroxyacetone side chain.

In particular, this invention relates to a process for the direct esterification of a 17α-hydroxy group in a 3,20-dioxo-4-pregnene-17α,21-diol 21-hydrocarboncarboxylate by reaction thereof with an arylcarboxylic acid anhydride or halide and alkyl lithium at low temperatures whereby is obtained the corresponding 17α-arylcarboxylate. Said 17α-arylcarboxylates are useful as intermediates in preparing pharmacologically active steroids having anti-inflammatory activity.

2. Prior Art

In Breslow et al., U.S. Pat. No. 4,252,719 and in U.S. Pat. No. 4,260,464 are described the use of 17α-iodobenzoate esters of 9,11-unsubstituted steroids of the pregnane series to prepare the corresponding 9α-chloro derivatives useful as anti-inflammatory agents or as intermediates in the preparation of other anti-inflammatory steroids.

The prior art methods for preparing the requisite 17α-iodobenzene carboxylates described in U.S. Pat. Nos. 4,252,719 and 4,260,464 comprise reaction of the corresponding 17α-hydroxy steroid with an iodoaryl substituted reagent (preferably m-iodobenzoyl chloride) and an amine (e.g. pyridine or dimethylaminopyridine) in an organic solvent at elevated temperatures in an inert atmosphere.

This method, however, when applied to steroids having a dihydroxyacetone side chain, particularly to such steroids having a 16β-methyl group, results in mixtures of products from which it is difficult to isolate the desired 17-ester.

By out invention, we have developed a novel method of directly converting a 17α-hydroxy group in a steroid of the pregnane series having a dihydroxyacetone side chain to the corresponding 17α-arylcarboxylate ester with minimal side reactions whereby is produced good yield of the 17α-arylcarboxylate ester substantially free by-products. Additionally, our esterification process advantageously is completed within a relatively short time as compared to prior art methods (e.g. in 4 hours, versus 22 hours for the U.S. Pat. No. 4,260,464 process). Our invention is particularly useful in preparing the 17α-iodocarboxylate ester of 16β-methyl-1,4-pregnadiene-17α,21-diol-3,20-dione 21-benzoate, a valuable intermediate in the manufacture of betamethasone.

DESCRIPTION OF INVENTION

Our invention relates to a process for preparing a steroid ester selected from the group consisting of a 4-pregnene of formula I

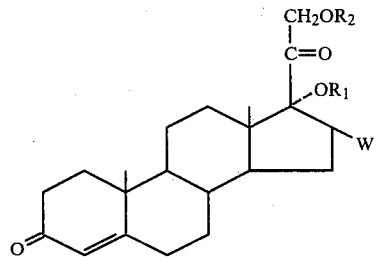

wherein
  $R_1$ is an acyl radical of a hydrocarboncarboxylic acid containing an aryl group having up to 12 aromatic carbon atoms and which may be substituted by halogeno, methyl, or methoxy;
  $R_2$ is an acyl radical of a lower alkanoic acid, or benzoic acid and methyl-substituted derivatives thereof,
  W is hydrogen or β-methyl; and
  the 1-dehydro, 6-dehydro, and 1,6-dehydro analogs thereof;

which comprises the reaction of a compound of formula II

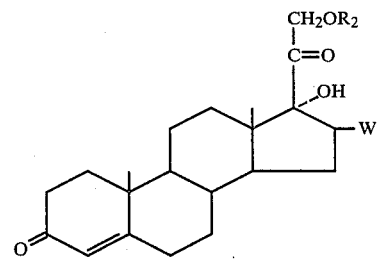

wherein W and $R_2$ are as defined hereinabove, and the 1-dehydro, 6-dehydro, and 1,6-bis-dehydro analogs thereof, with lower alkyl lithium, a reagent selected from the group consisting of $(R_1)_2O$ and $R_1X$ wherein $R_1$ is as hereinabove defined and X is chlorine, bromine or iodine, and a 4-(di-lower alkyl)aminopyridine in a non-reactive solvent at temperatures in the range of from about $-40°$ C. to about $-80°$ C.

As used in the specification and claims of this application, "halogeno" refers to fluoro, chloro, bromo and iodo.

The term "acyl" as used in $R_1$ and $R_2$ denotes a radical derived from an acid by removal of a hydroxyl group; e.g. acetyl is the acyl radical of acetic acid, and benzoyl is the acyl radical of benzoic acid.

The acyl radicals of the compounds of the invention as defined by $R_1$ in formula I above include those derived from aryl carboxylates having up to 12 carbon atoms, such as benzoyl and biphenylcarboxoyl, and the halogeno, methyl, and methoxy-substituted derivatives thereof. Examples of the substituted acyl radicals include p-fluorobenzoyl, p-methoxybenzoyl, m-iodobenzoyl, p-iodophenylacetyl, m-iodophenylacetyl, m-iodophenylpropionyl, and 4'-iodo-3-biphenylcarboxoyl, with m-iodobenzoyl being preferred.

The acyl radicals defined by $R_2$ in formula I include acyl radicals of lower alkanoic acids wherein "lower alkanoic" refers to aliphatic carboxylic acids having 1–8 carbon atoms (e.g. formic, acetic, propionic, trimethyl acetic, butyric, isobutyric, valeric, isovaleric, caproic, tert.-butylacetic, enanthic, and caprylic acids), and benzoic acid and methyl-substituted benzoic acids such as toluic and dimethyl benzoic. The preferred $R_2$ group is benzoyl.

Lower alkyl groups included within the definition of lower alkyl lithium and 4-(di-lower alkyl)aminopyridine refer to alkyl groups having up to 4 carbon atoms, e.g. methyl, ethyl, n-propyl, iso-propyl, n-butyl, sec.-butyl, and tert.-butyl. Preferred are n-butyl lithium and 4-dimethylaminopyridine.

The reagents $(R_1)_2O$, and $R_1X$ are anhydrides and acyl halides containing the acyl radicals, $R_1$, defined above, e.g. m-iodobenzoic anhydride, and m-iodobenzoyl chloride.

Non-reactive solvents useful for our process include those non-hydroxylated, non-polar, water-miscible organic solvents which are liquids in the required temperature range of from about $-40°$ C. to about $-80°$ C. "Non-reactive" refers to solvents which do not react with the starting material in competing side-reactions, and "non-hydroxylated" refers to solvents which do not contain a hydroxy group. Typical solvents for this invention are ethers, a preferred solvent being tetrahydrofuran.

In our process the reaction of the lower alkyl lithium reagent with the steroid hydroxy group selectively converts the 17-hydroxy group to the lithium steroidal alkoxide without attacking ketone groups present on the steroid. The 17-lithium alkoxide thus produced reacts with the acid reagent to produce the desired 17-arylcarboxylate ester in good yield.

The low temperature of the reaction, e.g. about $-40°$ C. to about $-80°$ C., helps to eliminate any migration of the 21-ester group to the 17-position which occurs at higher temperatures. The addition of the 4-(di-lower alkyl)aminopyridine also promotes acylation at the 17-position over rearrangement of the 21-ester group, as does the use of a non-polar solvent. By eliminating migration of the 21-ester group of the starting steroid, the yield of the desired 17-arylcarboxylate ester is increased.

Additionally, our process requires only one-third to one-fourth of the 4-(di-lower alkyl)aminopyridine used in prior art methods for direct esterification at the 17α-position.

A preferred method for carrying out the process of our invention comprises the reaction of the 17-hydroxy steroid of formula II with n-butyl lithium, an reagent selected from the group consisting of $(R_1)_2O$ and $R_1X$, and 4-dimethylaminopyridine in tetrahydrofuran at $-78°$ C. under an inert atmosphere (e.g. nitrogen, argon). The preferred ratios of reagent to steroid are in the range of 3 to 1 moles of $(R_1)_2O$ or $R_1X$ per mole of steroid, 0.5 to 1 mole of 4-(di-lower alkyl)aminopyridine per mole of steroid, and 0.5 to 2 moles alkyl lithium per mole of steroid. The n-butyl lithium and the anhydride or acyl halide reagent may be added simultaneously or consecutively in either order, but better yields are obtained when the n-butyl lithium is added first.

Preferred reagents $(R_1)_2O$ and $R_1X$ for our process are derived from m-iodobenzoic acid, m-iodobenzoyl chloride being particularly preferred, especially where the desired product of formula I will be used as an intermediate and subsequently chlorinated by the Breslow method of U.S. Pat. No. 4,252,719.

A preferred starting material for our process is a steroid of formula II wherein $R_2$ is benzoyl (e.g. 16β-methyl-1,4-pregnadiene-71α,21-diol-3,20-dione 21-benzoate), particularly where the desired product is a 17α-iodobenzoate ester. The presence of the 21-benzoyl group not only minimizes rearrangement during esterification of the 17-hydroxy group, but exhibits additional advantages when preparing the corresponding 9α-chloro derivative via the method in the above-mentioned Breslow U.S. Pat. No. 4,252,719: the chlorination of a 17-arylcarboxylate 21-benzoate is faster and cleaner than that of the corresponding 17-arylcarboxylate 21-alkanoate, and requires less halogenating reagent.

A particularly preferred embodiment of our invention comprises the reaction of 16β-methyl-1,4-pregnadiene-17α, 21-diol-3,21-dione 21-benzoate in tetrahydrofuran at $-78°$ C. in an inert atmosphere with n-butyl lithium, 4-dimethylaminopyridine and m-iodobenzoyl chloride at molar ratios relative to the steroid of 1.2, 0.6 and 2.0, respectively, whereby 16β-methyl-1,4-pregnadiene-17α,21-diol-3,20-dione 17-m-iodobenzoate 21-benzoate is obtained in high yield.

All 17-iodobenzoate esters produced by our process are useful as intermediates in the preparation of the corresponding 9α-chloro-17α-iodobenzoate esters, which in turn are useful in preparing other 9α-halo-11β-hydroxy corticoids via known procedures (e.g. betamethasone, 9α-fluoro-16β-methyl-1,4-pregnadiene-11β,17,21-triol-3,20-dione). The 17-benzoate esters produced by our process are also useful intermediates for preparing anti-inflammatory corticoids via known procedures.

By way of illustration of our invention, the following non-limiting example of the preferred mode of our process is given.

PREPARATION 1

16β-Methyl-1,4-Pregnadiene-17α,21-Diol-3,20-Dione 21-Benzoate

A. Dissolve 16β-methyl-1,4-pregnadiene-17α,21-diol-3,20-dione (71.7g., 0.2 mole) in pyridine (700 ml), add benzoyl chloride (56.4 g., 0.4 mole) in pyridine (340 ml) at a rate which allows the temperature to be maintained at less than 25° C., and stir for 30 minutes.

Slowly and with stirring pour the reaction mixture into 10.4 liters of a 10% aqueous hydrochloric acid solution. Filter the precipitate and repeatedly wash the filter cake with distilled water, then dry in a draft oven at 50° C. Purify the resultant residue by recrystallizing from isopropanol (4.75 liters); cool the solution to room temperature with stirring, filter the solid, wash with ice cold isopropanol (100 ml), and dry the solid in a draft oven at 50° C. to obtain purified title product.

B. Alternatively, cool a mixture of 16β-methyl-1,4-pregnadiene-17α,21-diol-3,20-dione (3.58 g., 0.01 mole), tetrabutylammonium bromide (0.32 g., 0.001 mole), methylene chloride (20 ml), and aqueous sodium hydroxide (5 ml of a 30% solution) to $-5°$ to 0° C. Add dropwise with stirring a solution of benzoyl chloride (1.97 g., 0.014 mole) in methylene chloride (2 ml), maintaining the temperature below 0° C.: continue to stir at less than 0° C. for 50 minutes.

To extract the product, add methylene chloride (30 ml) and water (30 ml), then separate the organic phase and wash with 3×25 ml water (until washings are neutral). Dry the organic phase over anhydrous sodium sulfate and evaporate the solvent in vacuo. Triturate the resultant product with hexane, filter the solid and dry in a draft oven at 50° C. Further purify the resultant residue by recrystallization from isopropanol to obtain purified 16β-methyl-1,4-pregnadiene-17α,21-diol-3,20-dione 21-benzoate.

EXAMPLE 1

16β-Methyl-1,4-Pregnadiene-17α,21-Diol-3,20-Dione 17-m-Iodobenzoate 21-Benzoate Dissolve 16β- methyl-1,4-pregnadiene-17α,21-diol-3,20-dione 21-benzoate (1.16 g., 2.5 mmol) and 4-dimethylaminopyridine (0.18 g., 1.5 mmol) in dry tetrahydrofuran (40 ml). Cool the mixture to −78° C. under a nitrogen atmosphere and, maintaining the temperature below −75° C., slowly add n-butyl lithium (1.88 ml of a 1.6 N solution in hexanes, 3.0 mmol) and stir for 15–20 minutes. Still maintaining the −75° C. temperature, add dropwise a solution of m-iodobenzoyl chloride (1.33 g., 5.0 mmol) in dry tetrahydrofuran (3 ml). Continue stirring at −75° C. for four hours during which time the desired 17α-m-iodobenzoate ester precipitates.

Pour the resultant reaction mixture into 600 ml distilled water with stirring. Extract the gummy product twice with 75 ml methylene chloride. Wash the combined organic layers twice with 75 ml aqueous saturated sodium bicarbonate solution. Dry the organic layer over anhydrous sodium sulfate and evaporate the solvent in vacuo.

Purify the crude product further by column chromatography on silica gel (22 g. of 60–200 mesh) using 2.5 liters of methylene chloride to elute the column. Combine the desired fractions as determined by thin-layer chromatography on silica gel eluted by methylene chloride:ethyl acetate (10:1) and visualized by ultraviolet light or charring. Evaporate the solvent in vacuo to obtain pure 16β-methyl-1,4-pregnadiene-17α,21-diol-3,20-dione 17-m-iodobenzoate 21-benzoate, m.p. 171°–178° C. Yield—75% theory.

EXAMPLE 2

Conversion of Product of Example 1 to the Corresponding 9α-Chloro Derivative Dissolve 16β-methyl-1,4-pregnadiene-17α,21-diol-3,20-dione 17-m-iodobenzoate 21-benzoate (2.08 g., 3.0 mmol) with stirring in methylene chloride (150 ml) and add iodobenzene dichloride (1.24 g., 4.5 mmol). Cool in an ice bath to a temperature below 20° C., and while maintaining that temperature, illuminate the reaction mixture at a distance of 15 cm with a 275 watt G.E. sunlamp for two hours. The progress of the reaction may be monitored by thin-layer chromatography on silica gel with ether:hexane (2:1) as developing solvent.

Wash the reaction product with 2×50 ml sodium thiosulfate (5% solution) followed by 50 ml water. Dry the organic phase over anhydrous sodium sulfate, filter and evaporate the solvent in vacuo. Triturate the resultant residue with hexane (30 ml), then filter the resultant solid and wash with hexane to produce 9α-chloro-16β-methyl-1,4-pregnadiene-17α,21-diol-3,20-dione 17-m-iodobenzoate 21-benzoate. Yield—85%.

To purify the above product further, dissolve the solid product (1.4 g) in methylene chloride (10 ml) and bring to reflux. Add methanol (20 ml) until the reaction mixture is cloudy. Cool the mixture with stirring, filter, and wash the resultant residue sparingly with cold methanol. Repeat the entire reflux procedure twice to obtain the purified product.

We claim:

1. A process for preparing a steroid ester selected from the group consisting of 4-pregnenes of formula I

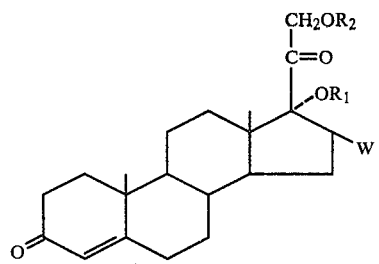

wherein
- R$_1$ is an acyl radical of a hydrocarboncarboxylic acid containing an aryl group having up to 12 aromatic carbon atoms and which may be substituted by halogeno, methyl, or methoxy;
- R$_2$ is an acyl radical of a lower alkanoic acid or benzoic acid and methyl-substituted derivatives thereof;
- W is hydrogen or β-methyl; and
- the 1-dehydro, 6-dehydro and 1,6-bis-dehydro analogs thereof;

which comprises the reaction of a 17α-hydroxy steroid selected from the group consisting of a 4-pregnene of formula II

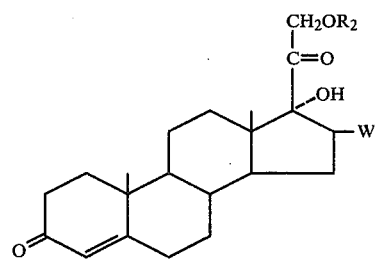

wherein
W and R$_2$ are as defined hereinabove;
and the 1-dehydro, 6-dehydro, and 1,6-bis-dehydro analogs thereof;
with lower alkyl lithium, a reagent selected from the group consisting of (R$_1$)$_2$O, and R$_1$X, wherein R$_1$ is as hereinabove defined and X is chlorine, bromine or iodine, and a 4-(di-lower alkyl)aminopyridine in a nonreactive solvent at temperatures in the range of from about −40° C. to about −80° C.

2. A process of claim 1 wherein the solvent is tetrahydrofuran, the 4-(di-lower alkyl)aminopyridine is 4-dimethylaminopyridine, the alkyl lithium is n-butyl lithium, and the reaction is carried out at −78° C.

3. A process of claim 2 wherein R$_1$X is m-iodobenzoyl chloride.

4. A process of claim 2 or 3 wherein the starting material is a 1,4-dehydro analog of formula II wherein W is β-methyl.

5. A process of claim 3 wherein the starting material is a 1,4-dehydro analog of formula II wherein R$_2$ is benzoyl and W is β-methyl, whereby is obtained 16β-methyl-1,4-pregnadiene-17α,21-diol-3,20-dione 17α-m-iodobenzoate 21-benzoate.

* * * * *